United States Patent [19]

Bundy

[11] 4,129,727

[45] Dec. 12, 1978

[54] 9-DEOXY-9-METHYLENE-PGF$_1$-PYRROLIDYLAMIDES

[75] Inventor: Gordon L. Bundy, Portage, Mich.

[73] Assignee: The Upjohn Company, Kalamazoo, Mich.

[21] Appl. No.: 894,273

[22] Filed: Apr. 7, 1978

Related U.S. Application Data

[63] Continuation-in-part of Ser. No. 786,250, Apr. 11, 1977, Pat. No. 4,098,805.

[51] Int. Cl.$^2$ .......................................... C07C 177/00
[52] U.S. Cl. ................................... 542/426; 542/429; 260/326.4; 260/326.5 J

[58] Field of Search .............................. 542/426, 429; 260/326.4, 324.5 J

[56] References Cited

PUBLICATIONS

Derwent Abstract 16389U–B NL 7211860–Q 03/05/73.
Derwent Abstract 7550x/40 U.S. 3981868 09/21/76.

*Primary Examiner*—Paul J. Killos
*Attorney, Agent, or Firm*—Robert A. Armitage

[57] ABSTRACT

The present invention relates to novel 9-deoxy-9-methylene-PGF$_1$-pyrrolidylamides. These compounds are useful pharmacological agents, and are useful for the same purposes as the corresponding 9-deoxy-9-methylene-PGF-type acids.

32 Claims, No Drawings

9-DEOXY-9-METHYLENE-PGF$_1$-PYRROLIDYLAMIDES

CROSS REFERENCE TO RELATED APPLICATIONS

This application is a continuation-in-part of Ser. No. 786,250, filed Apr. 11, 1977, now U.S. Pat. No. 4,098,805, issued July 4, 1978.

The present invention relates to novel 9-deoxy-9-methylene-PGF$_1$-pyrrolidylamides, the essential material constituting a disclosure of which is incorporated by reference from U.S. Pat. No. 4,098,805.

I claim:

1. A prostaglandin analog of the formula

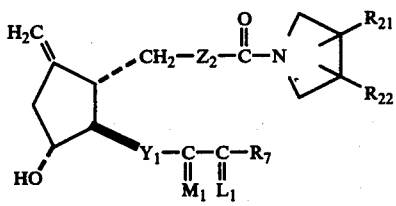

wherein Y$_1$ is trans—CH=CH—, —C|C—, or —CH$_2$CH$_2$— wherein M$_1$ is

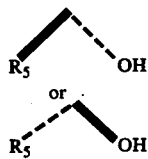

wherein R$_5$ is hydrogen or methyl;
wherein L$_1$ is

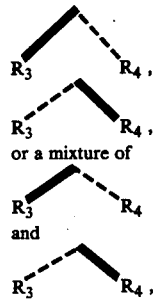

wherein R$_3$ and R$_4$ are hydrogen, methyl, or fluoro, being the same or different, with the proviso that one of R$_3$ and R$_4$ is fluoro only when the other is hydrogen or fluoro;
wherein Z$_2$ is
(1) —(CH$_2$)$_3$—(CH$_2$)$_g$—CH$_2$—,
(2) —(CH$_2$)$_3$—(CH$_2$)$_g$—CF$_2$—,
(3) —CH$_2$—O—CH$_2$—(CH$_2$)$_g$—CH$_2$—,
(4) —C|C—CH$_2$—(CH$_2$)$_g$—CH$_2$—,
(5) —CH$_2$—C|C—(CH$_2$)$_g$—CH$_2$—, (6) 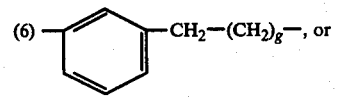, or (7) 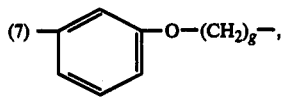, wherein g is 1, 2 or 3;
wherein R$_7$ is
(1) —(CH$_2$)$_m$—CH$_3$, (2) 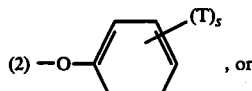, or (3) 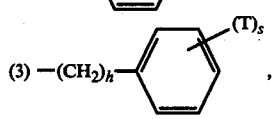, wherein m is 1 to 5, inclusive, h is 0 or 1, T is chloro, fluoro, trifluoromethyl, alkyl of 1 to 3 carbon atoms, inclusive, or alkoxy of 1 to 3 carbon atoms, inclusive, and s is 0, 1, 2, or 3, the various T's being the same or different, with the proviso that not more than two T's are other than alkyl, with the further proviso that R$_7$ is

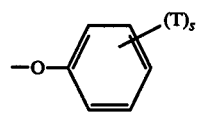

wherein T and s are as defined above, only when R$_3$ and R$_4$ are hydrogen or methyl, being the same or different; and
wherein R$_{21}$ and R$_{22}$ are hydrogen, alkyl of 1 to 12 carbon atoms, inclusive: aralkyl of 7 to 12 carbon atoms, inclusive, phenyl, phenyl substituted with 1, 2, or 3 chloro or alkyl of 1 to 3 carbon atoms, inclusive, or phenyl substituted with hydroxycarbonyl or alkoxycarbonyl of 1 to 4 carbon atoms, inclusive.

2. A prostaglandin analog according to claim 1, wherein Y$_1$ is —C|C—.

3. 9-Deoxy-9-methylene-13,14-didehydro-PGF$_1$, pyrrolidylamide, a prostaglandin analog according to claim 2.

4. A prostaglandin analog according to claim 1, wherein Y$_1$ is —CH$_2$CH$_2$—.

5. 9-Deoxy-9-methylene-13,14-dihydro-PGF$_1$, pyrrolidylamide, a prostaglandin analog according to claim 4.

6. A prostaglandin analog according to claim 1, wherein Y$_1$ is trans—CH=CH—.

7. A prostaglandin analog according to claim 6, wherein Z$_2$ is aromatic.

8. 9-Deoxy-9-methylene-3,7-inter-m-phenylene-3-oxa-4,5,6-trinor-PGF$_1$, pyrrolidylamide, a prostaglandin analog according to claim 7.

9. 9-Deoxy-9-methylene-3,7-inter-m-phenylene-4,5,6-trinor-PGF$_1$, pyrrolidylamide, a prostaglandin analog according to claim 7.

10. A prostaglandin analog according to claim 6, wherein Z$_2$ is aliphatic.

11. A prostaglandin analog according to claim 10, wherein M$_1$ is

12. 15-epi-9-deoxy-9-methylene-PGF$_1$, pyrrolidylamide, a prostaglandin analog according to claim 11.

13. A prostaglandin analog according to claim 10, wherein M$_1$ is

14. A prostaglandin analog according to claim 13, wherein Z$_2$ is cis—CH=CH—CH$_2$—(CH$_2$)$_g$—CH$_2$—.

15. A prostaglandin analog according to claim 14, wherein R$_7$ is

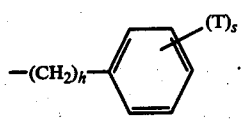

16. 9-Deoxy-9-methylene-17-phenyl-18,19,20-trinor-PGF$_1$, pyrrolidylamide, a prostaglandin analog according to claim 15.

17. A prostaglandin analog according to claim 14, wherein R$_7$ is

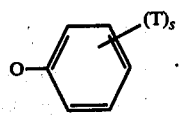

18. 9-Deoxy-9-methylene-16-phenoxy-17,18,19,20-tetranor-PGF$_1$, pyrrolidylamide, a prostaglandin analog according to claim 17.

19. A prostaglandin analog according to claim 14, wherein R$_7$ is —(CH$_2$)$_m$—CH$_3$.

20. A prostaglandin analog according to claim 19, wherein m is 3.

21. A prostaglandin analog according to claim 20, wherein g is 3.

22. 2a,2b-Dihomo-9-deoxy-9-methylene-15-methyl-PGF$_1$, pyrrolidylamide, a prostaglandin analog according to claim 21.

23. A prostaglandin analog according to claim 20, wherein g is 1.

24. A prostaglandin analog according to claim 23, wherein at least one of R$_3$ and R$_4$ is methyl.

25. 9-Deoxy-9-methylene-16,16-dimethyl-PGF$_1$, pyrrolidylamide, a prostaglandin analog according to claim 24.

26. A prostaglandin analog according to claim 23, wherein at least one of R$_3$ and R$_4$ is fluoro.

27. 9-Deoxy-9-methylene-16,16-difluoro-PGF$_1$, pyrrolidylamide, a prostaglandin analog according to claim 26.

28. A prostaglandin analog according to claim 23, wherein R$_3$ and R$_4$ are both hydrogen.

29. A prostaglandin analog according to claim 28, wherein R$_5$ is methyl.

30. 9-Deoxy-9-methylene-15-methyl-PGF$_1$, pyrrolidylamide, a prostaglandin analog according to claim 29.

31. A prostaglandin analog according to claim 28, wherein R$_5$ is hydrogen.

32. 9-Deoxy-9-methylene-PGF$_1$, pyrrolidylamide, a prostaglandin analog according to claim 31.

* * * * *

UNITED STATES PATENT AND TRADEMARK OFFICE
CERTIFICATE OF CORRECTION

PATENT NO. : 4,129,727
DATED : December 12, 1978
INVENTOR(S) : Gordon L. Bundy

It is certified that error appears in the above-identified patent and that said Letters Patent are hereby corrected as shown below:

Column 1, line 28 and 62 and 63, "-C|C-" should read -- -C≡C- --;
Column 2, line 46, "-C|C-" should read -- -C≡C- --.

Signed and Sealed this

Tenth Day of July 1979

[SEAL]

Attest:

LUTRELLE F. PARKER
Attesting Officer    Acting Commissioner of Patents and Trademarks